United States Patent [19]

Schneider

[11] Patent Number: 5,507,460
[45] Date of Patent: Apr. 16, 1996

[54] TUBING HOLDER ESPECIALLY FOR PATIENT APPLICATIONS

[75] Inventor: Eberhard Schneider, Halver, Germany

[73] Assignee: P.C. Turck GmbH & Co. KG, Ludenscheid, Germany

[21] Appl. No.: 232,930

[22] Filed: Apr. 25, 1994

[30] Foreign Application Priority Data

Apr. 23, 1993 [DE] Germany ............... 43 13 329.0
Nov. 16, 1993 [DE] Germany ............... 43 38 900.7

[51] Int. Cl.$^6$ ........................... F16L 3/08
[52] U.S. Cl. ............... 248/225.21; 248/73; 248/339; 248/304; 24/601.2
[58] Field of Search ............... 248/73, 61, 215, 248/221.4, 225.1, 225.2, 290, 301, 303, 304, 339; 24/72.5, 339, 343, 324, 662, 601.2

[56] References Cited

U.S. PATENT DOCUMENTS

| | | | |
|---|---|---|---|
| 810,004 | 1/1906 | Tabler | 24/343 |
| 3,747,166 | 7/1973 | Eross | 24/81 |
| 4,049,905 | 9/1977 | Maranell | 24/601.2 |
| 4,599,767 | 7/1986 | Kasai | 24/601.2 |
| 4,617,704 | 10/1986 | Kasai | 24/601.2 |
| 4,665,592 | 5/1987 | Kasai | 24/601.2 |
| 4,680,837 | 7/1987 | Rubinstein | 24/601.2 |
| 4,707,906 | 11/1987 | Posey | 29/453 |
| 4,868,954 | 9/1989 | Kasai | 24/601.2 |
| 5,337,987 | 8/1994 | Sawatsky | 248/231.8 |

FOREIGN PATENT DOCUMENTS

| | | |
|---|---|---|
| 2350717 | 2/1977 | France . |
| 536519 | 5/1941 | United Kingdom ............... 248/61 |
| 576759 | 4/1946 | United Kingdom . |
| 963699 | 7/1964 | United Kingdom ............... 24/343 |

Primary Examiner—Karen J. Chotkowski
Assistant Examiner—Anita M. King
Attorney, Agent, or Firm—Herbert Dubno

[57] ABSTRACT

A holder for a medicinal tubing, electric cable or the like in the vicinity of a patient is connected by a swivel pin formation to a coupling member or support which is attached via a wire segment to some object, the support being able to swing and slide on the wire segment.

12 Claims, 4 Drawing Sheets

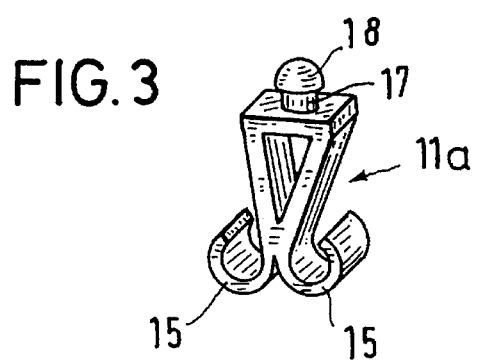
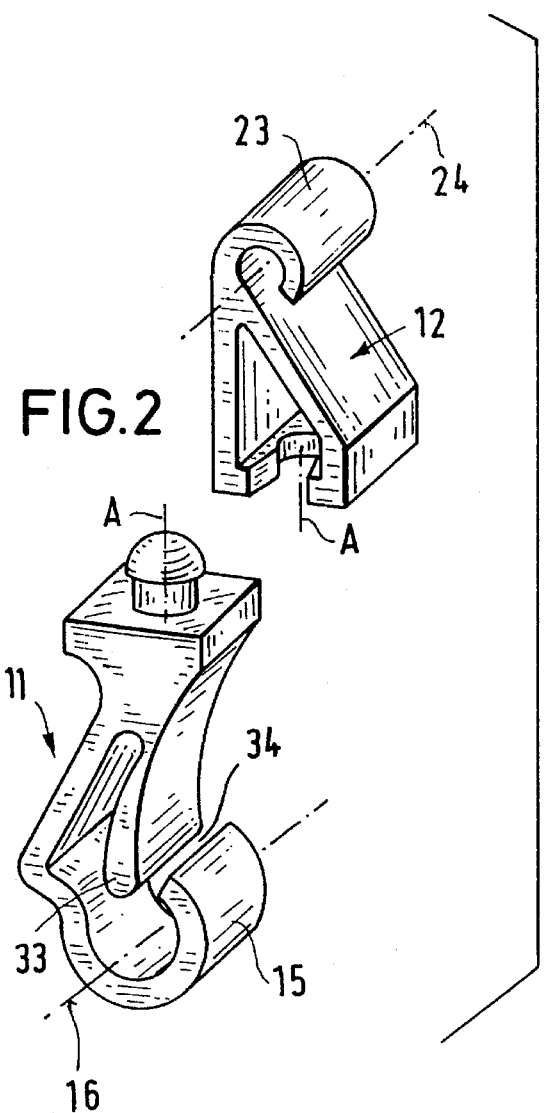
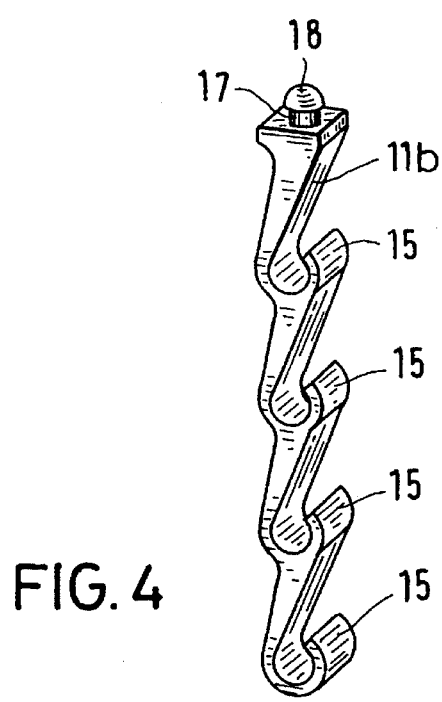

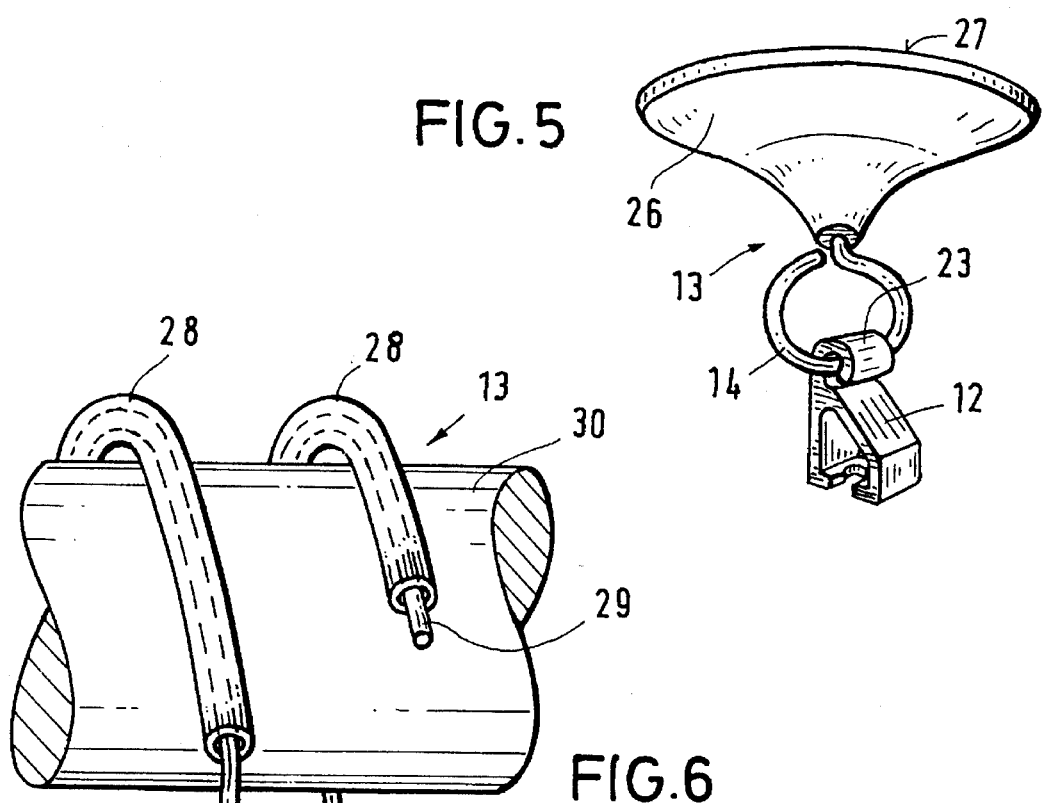
FIG. 5
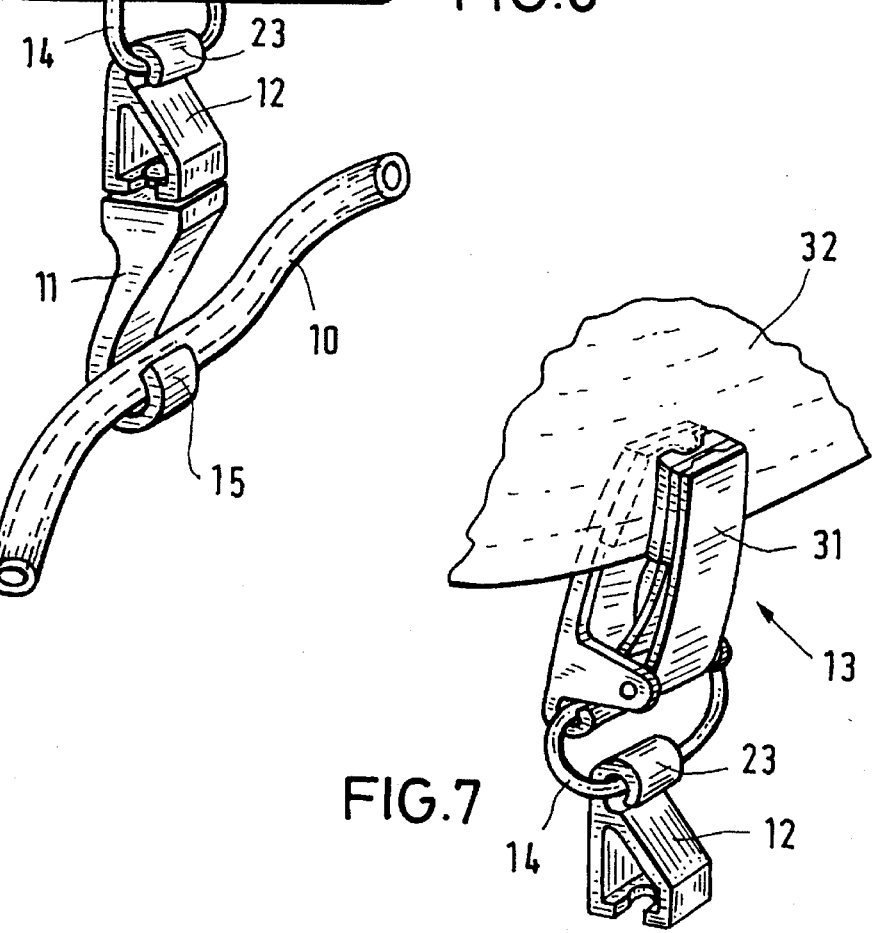
FIG. 6
FIG. 7

TUBING HOLDER ESPECIALLY FOR PATIENT APPLICATIONS

FIELD OF THE INVENTION

The present invention relates to a device for holding an elongated member, especially for medicinal technology and in a patient environment, the elongated member being tubing or other duct work or cabling. More particularly this invention relates to a holder for conductors and duct work like tubing, electrical cabling or the like on objects in medicinal technology and objects associated with the sick and aged, like beds, bed stands, bedding, patient clothing or the furnishings, equipment or hardware associated with a hospital, sick room or care facility.

BACKGROUND OF THE INVENTION

In care facilities like hospitals, old age homes or the like, medicinal duct work like infusion tubing, blood transfusion tubing and catheters are widely used. In such applications, electrical cabling, for example, telephone cabling, call button cabling and even electrical cabling for treatment or monitoring electronic devices may be required in the region of the patient and like the tubing may have to be held temporarily in place. Such elongated members are commonly held onto the bed, bed stand, bed clothing or patient garments and the furnishings in the region of the patient by adhesive tape or by pinning to the bed clothing. The means for holding the tubing and cabling in place is generally applied when and as necessary, utilizing the most convenient facilities at hand. Frequently, however, the technique used to temporarily hold the tubing or cabling in place does not take up the longitudinal strains which may be applied by the patient to the tubing or cabling, the tubing or cabling may pull out or strain a wound, or the holding means may otherwise be unreliable and prone to release.

OBJECTS OF THE INVENTION

It is therefore an object of the present invention to provide an improved device for holding an elongated member in medicinal technology, namely, a duct or conductors such as the aforementioned tubing and cabling, which requires a limited number of parts, is easily manipulated and ensures a reliable and secure retention of the elongated member in applications such as those described.

Another object of the invention is to provide an improved holder for tubing and cabling in a patient environment whereby drawbacks of techniques used heretofore are obviated.

SUMMARY OF THE INVENTION

These objects are attained, in accordance with the invention by providing an assembly which comprises a holder having a seat relieving the tension strain on the elongated member (tubing or cabling) retained thereby and so connected to a coupling piece or support so as to be free to rotate about an axis which is perpendicular to the seat part yet is axially fixed to that support, the support being in turn provided with a fastening or attachment means which has at least one wire like segment along which the support is free to move back and forth and on which the support can swing via an eye-like formation on the support.

More particularly, a device for holding an elongated member in medicinal technology can comprise:

a holder formed with a seat releasably engageable with the member to relieve longitudinal strain thereon, and a coupling formation defining an axis of rotation for the holder substantially perpendicular to the seat;

a support provided with a mating formation engageable with the mating formation and upon which the holder is supported by the formations, the formations enabling rotation of the holder about the axis while restricting separation of the formations along the axis, the support further having a fastening eye; and attachment means having at least an elongated segment on which the eye is freely slidable back and forth along the segment and on which the eye is freely swingable for securing the support to an object proximal to a patient.

The elongated member may be a duct or conductor like the tubing and electrical cabling described and the object to which the attachment means secures the eye can be any of the furnishings provided in the sick room or old age care facility like, bed, bed stand, patient garment or the like.

It will be apparent that, by contrast with conventional holders which have only the ability to fasten the elongated member to the particular object, the device of the invention has three parts which can interact. The first part, i.e. the holder itself serves for direct connection to the elongated member. The second part, to which the first part is connected by the formations described, serves for positioning the holder while allowing its rotation about the axis although not in axial movement along the axis relative to the support. The attachment means, in turn, connects the support to the object so that the supporting has freedom of movement along the attachment wire back and forth and freedom of swinging movement, while providing the rotation or swivel movement of the holder attached thereto.

The support thus acts as a coupling member providing all necessary degrees of freedom of movement for preventing this to the elongated member while taking up longitudinal strain thereon. The possibility that the elongated member will pull out, which is especially dangerous in the case of infusion tubing and blood transfusion tubing is minimized to the point that it is negligible.

An input advantage of the invention is the wide range of mobility permitted the elongated member while nevertheless retaining it in place.

For example, 360° mobility of the elongated member is permitted about an axis perpendicular to the longitudinal dimension of that member and the seat about the aforementioned axis. The elongated member can swing back and forth as well with the support on the wire portion of the attachment means and even from back to forth movement is permitted within the limits of this wire segment. However, beyond this mobility, the location of the attachment site of the elongated member is well defined.

The swivel action is effected between two formations as described which can be easily assembled and plug fitted one into the other, either in the axial direction or transversely thereto. This can easily be achieved with injection molded parts which do not have to be machined or shaped after injection molding.

A further degree of freedom is afforded by the fact that the attachment means enables the support to be secured on a bed frame or on the bedding, on the patients clothing or on any other object as desired and sensible. It should be noted, of course, that the ability of the device to swing and move back and forth in the manner described should be unimpeded.

A releasable connection between the holder and the support facilitates bed changing and allows in some cases the attachment means to be permanently mounted on an object. In that case, for example, the attachment means maybe an adhesive plate. More specifically, the formations can constitute an axially insertable plug and socket connection inseparable without tools. Alternatively, one of the formations can be formed with a detect into which the other formations is insertable transversely to the axis.

The seat can generally conform to the member, i.e. by cylindrical where the elongated member is tubing, can extend around the member through at least 180°, and can form a laterally open eye in which the member is insertable and clipped.

A spring tongue on the support can block escape of the member from the seat. The holder can be provided with a plurality of seats for respective elongated members either disposed one above another or along side one another and both the holder and the support can be parts ejection molded from synthetic resin. The attachment means can be a clamp, clip, especially a trouser clip, magnet, suction cup, wire loop, wire helix or clamp, or the adhesive plate mentioned previously.

BRIEF DESCRIPTION OF THE DRAWING

The above and other objects, features, and advantages will become more readily apparent from the following description, reference being made to the accompanying drawing in which:

FIG. 2 is an exploded perspective view illustrating another embodiment of the device again with the holder separated from its support;

FIG. 3 is a perspective view of another embodiment of the holder;

FIG. 4 is a perspective view of yet another holder for use in accordance with the invention;

FIGS. 5–7 are perspective views showing various attachment means for a device generally of the type shown in FIG. 1;

SPECIFIC DESCRIPTION

Figure 1:
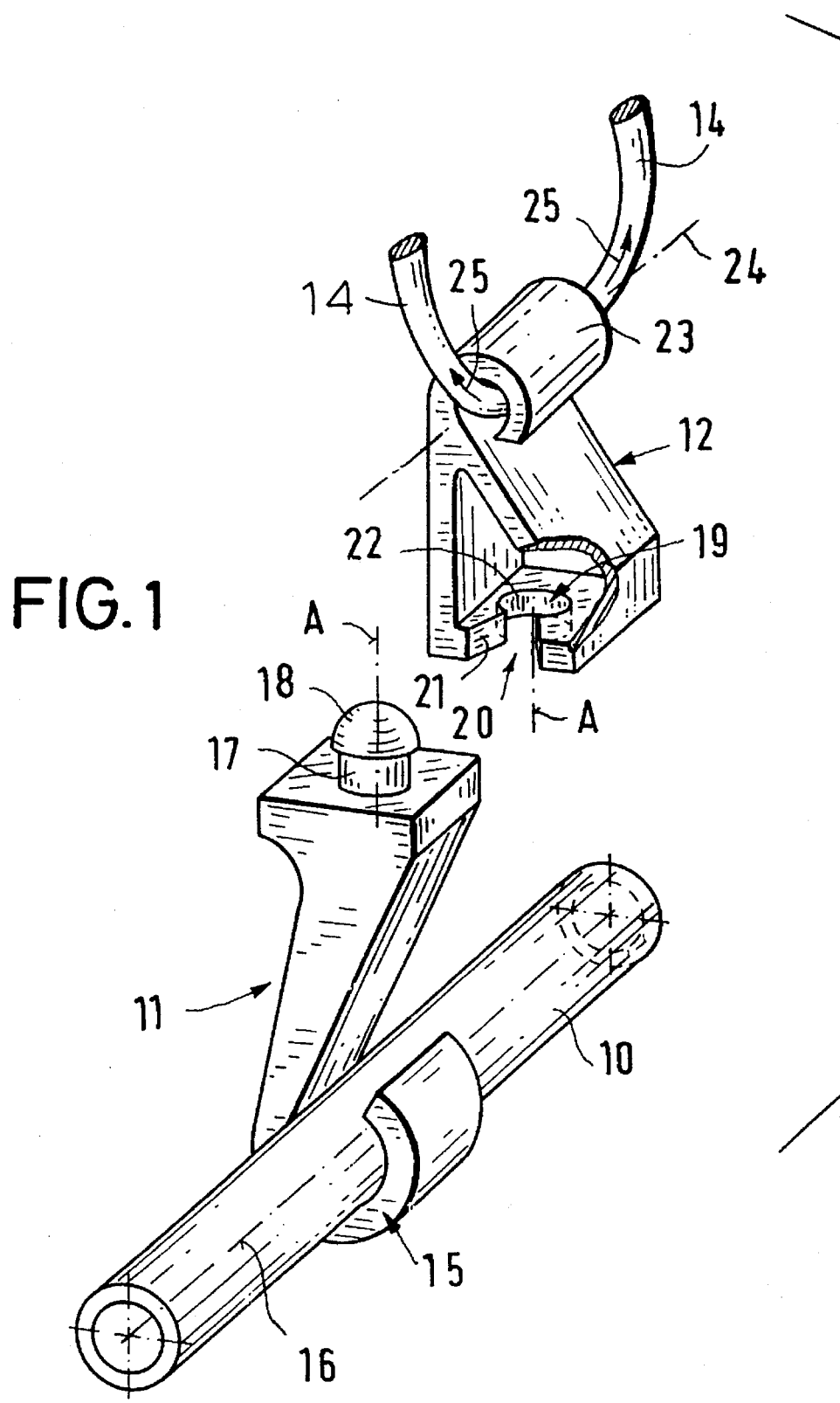
FIG. 1 is an exploded perspective view of a device according to the invention with the holder decoupled from its support.

As seen in FIG. 1 and in other FIGURES as well, an elongated member, such a medical tubing 10, for example, infusion tubing or blood transfer tubing, is shown to be engaged in a holder 11. In place of the tubing, an electric cable can be correspondingly engaged.

The holder 11 is connected by a coupling piece 12, referred to herein also as a support, to an attachment means 13 (FIGS. 5 to 7) which secures that support to an object with freedom of the swinging movement and back and forth movement only upon a wire segment 14 of the attachment means which is fragmentarily shown in FIG. 1.

The holder 11 is formed at one end with an eye onto the tubing 10 and thus retains the latter with a clamping action to relieve strain upon the tubing 10. The eye 15 is open at one side and extends around the tubing 10 by more than 180°. The tubing 10 can be clipped transversely in the laterally open eye.

It is desirable that the tubing 10 be engaged in the eye so that it can not slip longitudinally relative to the eye. The clamping action can be insured by making the internal diameter of the eye 15 somewhat smaller than the diameter of the outer periphery of the tubing 10.

At its other end, the holder 11 is formed with a pin 17 with a head 18. The longitudinal axis of the pin 17 forms a swivel axis for the holder 11 in the support 12. The support 12 has at its end turned toward the holder 11, a detent formation 19 into which the pin 17 can be inserted laterally. However, the head 18 prevents axial shifting of the holder 11 in the support 12.

The formation 19 has the configuration of a keyhole and is provided with an insertion slit 20 with inclined flanks 21 and an opening 22 in the wall of the formation 19. The width of the slit 20 at its narrowest point is thus slightly less than the diameter of the pin 17 although the diameter of the bore 22 is slightly greater but less than the diameter of the head 18.

Figure 8:
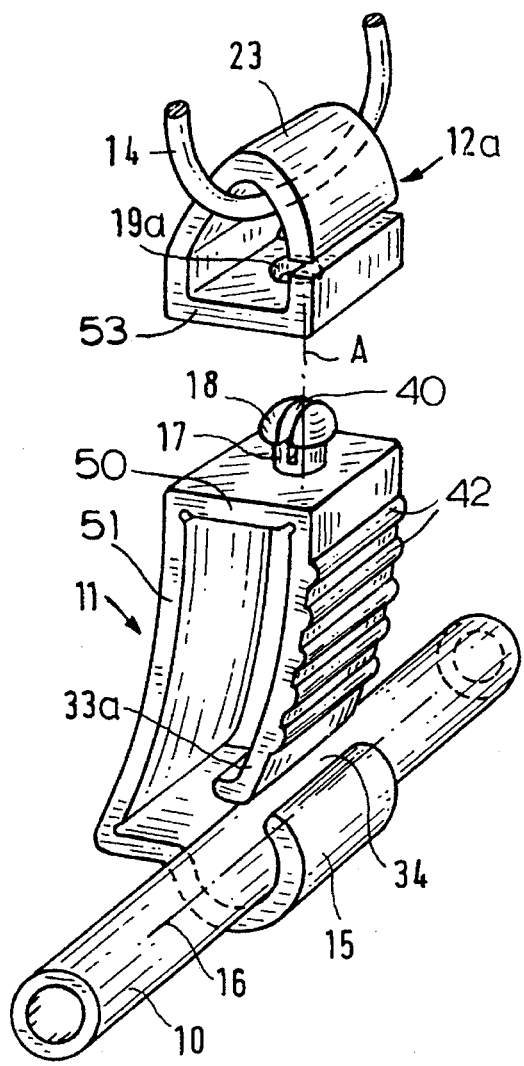
FIG. 8 is an exploded perspective view of yet another embodiment of the invention.
Figure 9:
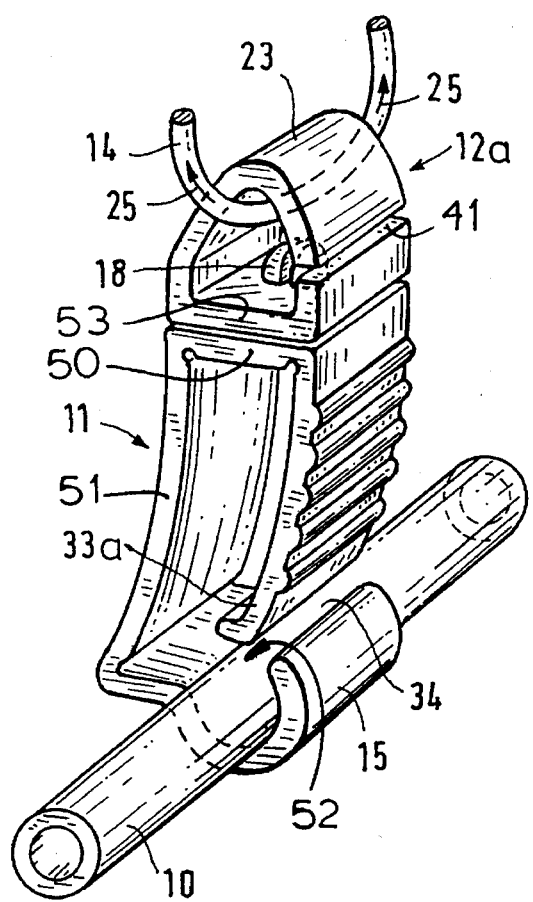
FIG. 9 is a perspective view of the device of FIG. 8 in its assembled form.

In FIGS. 8 and 9, the pin 17 and the head 18 are shown to be provided with a slit 40 so that the head halves can be pressed together as the pin is inserted axially into the formation 19 in a plug and socket engagement which cannot be released without tools, i.e. without pressing the head halves together.

Returning to FIG. 1 and the other FIGURES showing equivalent structures, it will be apparent that both the holder 11 and the coupling piece or support 12 can be injection molded parts of a thermoplastic synthetic resin having suitable elasticity, e.g. a nylon or other polyamide.

After the formations are joined, the holder 11 is free to rotate about the axis A on the support 12.

At the end of the support 12 opposite the holder 11, an eye 23 similar to the eye 15 is provided to engage the wire loop 14 which can be snapped laterally into the lateral open eye 23. The eye 23 allows the support 12 to swing freely from the wire loop 14 about a longitudinal axis 24 of the eye 23 and also permits some shifting of the eye 23 along the wire 14 in the longitudinal dimension of the wire and the eye as represented by the double arrow 25. The result is a pendulous mobility.

FIG. 2 shows an embodiment familiar to FIG. 1 wherein, however, the holder 11 is additionally provided with a spring tongue 33 party blocking the opening 34 into the eye 15. The member 10 can only be withdrawn from the eye 15 which has an axis 16 to which the axis A is perpendicular, only when the spring tongue 33 is deflected rearwardly.

The holder 11a shown in FIG. 3 has two eyes 15 deposited on opposite sides and hence side by side, for engagement with two pieces of tubing 10 a holder with four eyes 15 deposited one above the other for supporting 4 members in a parallel arrangement has been shown on the holder 11b of FIG. 4. Combinations of these two variants can also be made.

FIG. 5 shows a suction cup 26 or adhesive plate for the wire loop 14 or ring clipped into the eye 23 of the support 27. An adhesive foil, for example, a double backed adhesive foil can be provided at 27 to transform the suction cup into an adhesive plate.

From FIG. 6, it will be apparent that the attachment device 13 can be a rubber or silicone sheath 28 for a wire 29 which can be wound in a helix around a bedpost or bar 30, some other apparatus element or other fixtures in the hospital, old age home or care facility. In this case, the loop 14 is a portion of the wire from which the sheath 28 has been removed.

FIG. 7 shows an embodiment of the invention in which the wire loop 14 is provided in an eye of a clip, for example, a suspender clip 31 which can be attached to an object such as the bed clothing or a patients garment 32.

Finally, in FIGS. 8 and 9, we show an embodiment in which the wire loop 14 can be any of the wire segments illustrated in FIGS. 5 to 7 and passes through a support 12a in which the formation 19a is a hole in a tubular structure formed with a slit 41. The spring tongue 33a here can be provided with ribs 42 to enable it to be engaged more effectively by the thumb of the user. The spring tongue 33a extends downwardly from a plate portion 50 at the top of an upright portion 51 of the holder 11 so that the bottom of the tongue ends at the mouth 52 of the hook 15. The support 12a also has a plate portion at 53'. In all of the embodiments, once the tubing or cabling is clipped into the holder, the holders can be connected to the support which can have previously been attached at 13 to some object or can then be attached to the object.

I claim:

1. A device for holding an elongated member in medicinal technology, said device comprising:

a synthetic resin injection molded holder formed with a cylinder-segmental seat in the form of a hook extending over an arc in excess of 180° releasably engageable with said member to relieve longitudinal strain thereon, and a coupling formation defining an axis of rotation for said holder substantially perpendicular to said seat;

a synthetic resin injection molded. One-piece support provided with a mating formation engageable with said coupling formation and upon which said holder is supported by said formations, said formations enabling rotation of said holder about said axis while restricting separation of said formations along said axis and preventing any other relative movement of said holder and said support, said support further having an elongated fastening eye with a longitudinal slit therein, said formations forming an axially insertable plug and socket connection inseparable without tools; and attachment means including a wire loop having at least an elongated segment on which said eye is freely slidable back and forth along said segment and on which said eye is freely swingable for securing said support to an object proximal to a patient.

2. The device defined in claim 1, further comprising a spring tongue on said holder blocking escape of said member from said seat.

3. The device defined in claim 1 wherein said holder is provided with a plurality of said seats for respective members.

4. The device defined in claim 3 wherein said seats are disposed one above another.

5. The device defined in claim 3 wherein said seats are disposed one alongside another.

6. The device defined in claim 1 wherein said attachment means includes a clamp.

7. The device defined in claim 1 wherein said attachment means includes a clip.

8. The device defined in claim 1 wherein said attachment means includes a trouser clip.

9. The device defined in claim 1 wherein said attachment means includes a suction cup.

10. The device defined in claim 1 wherein said attachment means includes a wire helix.

11. The device defined in claim 1 wherein said attachment means includes a wire clamp.

12. A device for holding an elongated member in medicinal technology, comprising:

a holder injection molded in one piece from a synthetic resin and comprising a hook-shaped seat of cylindrical segmental configuration having a seat axis and extending in an arc around said axis through in excess of 180°, an upright portion extending upwardly from said seat, a plate portion at a top of the upright portion, and a spring tongue extending downwardly from said plate portion generally parallel to said upright portion toward a mouth of said seat and terminating above said mouth, said spring tongue being deflectable to enable insertion into said seat and removal therefrom of a member to be retained in said holder to relieve strain thereon, said tongue being formed with a multiplicity of parallel ribs, said plate portion being provided with a coupling formation constituted by a split pin projecting upwardly from said plate portion along a rotation axis perpendicular to said seat axis, said pin having a head;

a support formed as an elongated tube having a slit along one side of said tube, a plate portion along a bottom of said tube and a hole formed in said plate portion of said tube dimensioned to receive said pin so that said holder is retained by said support while being rotatable relative to said support exclusively about said rotation axis; and attachment means including a wire loop extending through said tube for securing said support to an object proximal to a patient, said tube forming an eye freely swingable on said loop.

* * * * *